United States Patent
Brelsford et al.

(10) Patent No.: US 9,804,078 B2
(45) Date of Patent: Oct. 31, 2017

(54) MULTIPLE COUPON APPARATUS FOR CATHODIC PROTECTION TESTING

(71) Applicant: Bass Corrosion Services, Inc., Longview, TX (US)

(72) Inventors: Randall Clay Brelsford, Longview, TX (US); Jordan Groody, White Oak, TX (US); Richard J. Smalling, Austin, TX (US)

(73) Assignee: Bass Corrosion Services, Inc., Longview, TX (US)

( * ) Notice: Subject to any disclaimer, the term of this patent is extended or adjusted under 35 U.S.C. 154(b) by 540 days.

(21) Appl. No.: 14/319,045

(22) Filed: Jun. 30, 2014

(65) Prior Publication Data

US 2015/0002132 A1 Jan. 1, 2015

Related U.S. Application Data

(60) Provisional application No. 61/841,856, filed on Jul. 1, 2013.

(51) Int. Cl.
*G01N 27/00* (2006.01)
*G01N 17/04* (2006.01)

(52) U.S. Cl.
CPC .................. *G01N 17/046* (2013.01)

(58) Field of Classification Search
CPC ...... G01N 17/046; G01N 17/04; G01N 27/00; G01N 27/70
USPC ................. 324/71.1, 347, 700, 425
See application file for complete search history.

(56) References Cited

U.S. PATENT DOCUMENTS

| 4,075,070 A * | 2/1978 | Du Bois | C22C 14/00 204/290.1 |
| 9,568,412 B2 * | 2/2017 | Kajiyama | G01N 17/02 |
| 2002/0194905 A1 * | 12/2002 | Moghissi | C23F 13/04 73/150 R |
| 2005/0006250 A1 * | 1/2005 | Russell | G01N 17/043 205/725 |
| 2006/0272434 A1 * | 12/2006 | Petrova | G01N 17/00 73/866 |
| 2011/0238347 A1 * | 9/2011 | Gemperli | C23F 13/04 702/65 |

* cited by examiner

*Primary Examiner* — Giovanni Astacio-Oquendo
(74) *Attorney, Agent, or Firm* — Jackson Walker L.L.P.

(57) ABSTRACT

A test coupon package suitable for a cathodic protection system includes a native test coupon and first and second active coupons. The active coupons may be biased with respect to the soil or other electrolytic medium in which a pipeline protected by the system resides. The first active coupon may have a surface area that will contact an electrolytic medium that is approximately equal to a surface area of the native test coupon that will contact the electrolytic medium. The surface area of the first active coupon may be substantially greater than a surface area of the second active coupon that will contact the electrolytic medium. The test coupon package may include an electrochemically stable reference electrode positioned between the first active coupon and the native coupon. The test coupon package may be substantially cylindrical and, in at least one embodiment, may include a conical nose connected to a first end of the test coupon package with the second active coupon attached to a narrow end of the conical nose.

15 Claims, 8 Drawing Sheets

MULTIPLE COUPON APPARATUS FOR CATHODIC PROTECTION TESTING

RELATED APPLICATIONS

This application claims priority to U.S. Application No. 61/841,856, filed Jul. 1, 2013, entitled Multiple Coupon Apparatus for Cathodic Protection Testing, which is incorporated in its entirety herein.

FIELD OF THE DISCLOSURE

The present disclosure relates to cathodic protection systems and, more particularly, systems for monitoring and testing cathodic protection systems and cathodically protected structures.

DESCRIPTION

Figure 1:
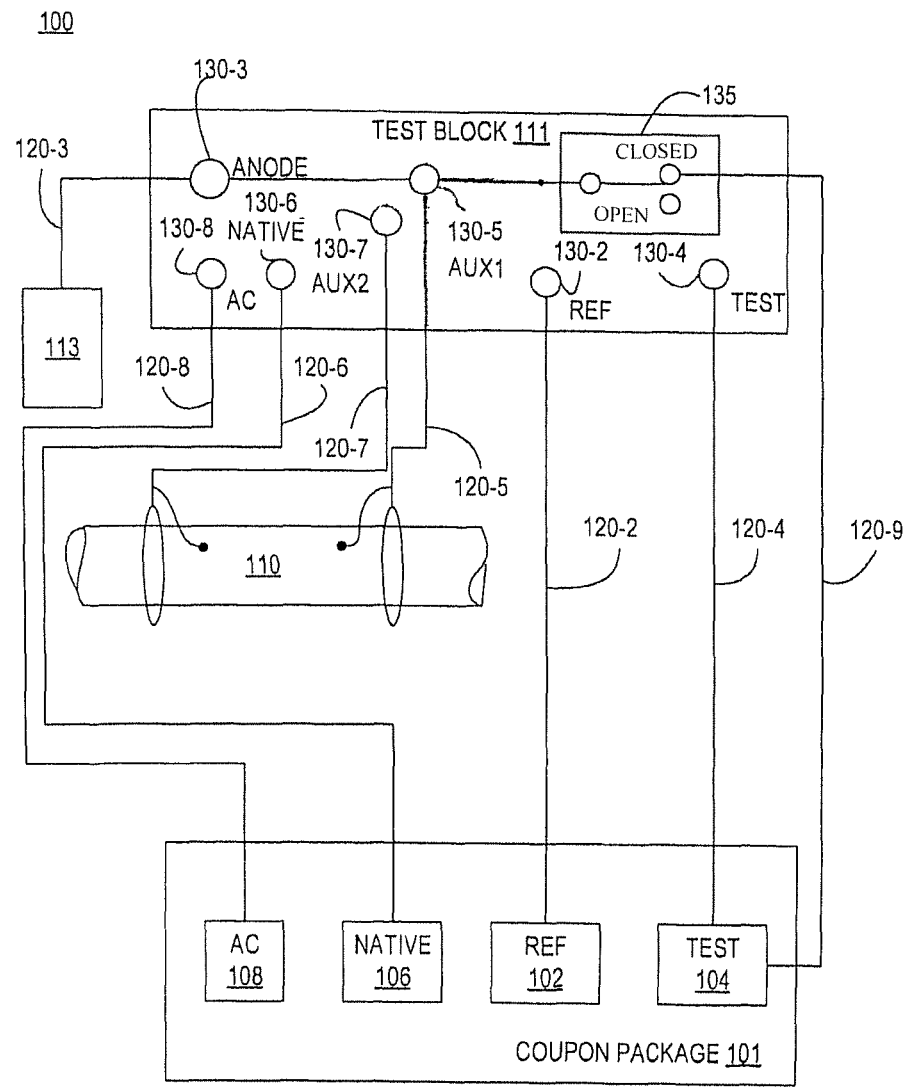
FIG. 1 illustrates a cathodic protection test system.

Metallic structures that are in contact with an electrolytic medium such as, for example, soil are susceptible to corrosion. A metallic structure may be coated as a primary measure to retard corrosion. Coatings for large structures such as steel pipelines inevitably include or develop defects or holidays that expose the metallic structure to the electrolytic medium. To address corrosion that would otherwise occur at a holiday, a cathodic protection system (CPS) creates an electrical current in opposition to a corrosion current that flows between the metallic structure and the electrolytic medium. An impressed current CPS includes an external DC power supply that biases the metallic structure relative to the electrolytic medium, changing the electrochemical state of the metallic structure and thereby preventing or slowing the corrosion process.

The voltage across the interface between the metallic structure and the electrolytic medium may be monitored to determine if adequate protection is being achieved. For applications in which the metallic structure is an underground steel pipeline and the electrolytic medium is the surrounding soil, the voltage across the interface is referred to as the "pipe-to-soil" potential. Various industry criteria may be used to determine acceptable values and variations of the pipe-to-soil potential. A common criterion requires a pipe-to-soil potential more negative than −0.85 V with respect to a suitable reference electrode, e.g., a copper-sulfate electrode, when the cathodic protection circuits are switched on. An IR voltage drop that occurs in the electrolyte and creates a discrepancy between the measured value and the actual potential at the interface may be quantified to obtain a more accurate measurement of the pipe-to-soil potential by performing "instant off" measurements of the potential, where the "instant off" potential is the potential measured just after the cathodic protection circuits are disabled, e.g., within approximately 1 second of the circuits being disabled.

Cathodic protection testing may include the testing of electrical characteristics of another structure, referred to as a coupon, that is positioned in close proximity to the protected structure. In the case of buried steel pipelines, as an example, a coupon may be made of the same or similar material as the pipeline, but is substantially smaller than the pipeline. In some implementations, the surface area of a coupon that will contact the electrolytic medium when installed is intended as an approximation of the surface area of known or suspected holidays occurring along a given length of pipe. When a coupon is intended to represent holidays occurring on the pipeline, the coupon is generally not coated, but receives the same cathodic protection that the pipeline receives. To establish a baseline for comparing any measured changes in the electrical characteristics of the coupon, a second coupon, physically identical or similar to the cathodically protected coupon, but electrically isolated from the cathodic protection system, may be desirable. A coupon that is electrically connected to the protected structure during operation of the CPS associated with the structure or during a portion of the testing may be referred to herein as an "active coupon" or "test coupon" while an electrically isolated coupon may be referred to herein as a "native coupon."

Pipelines and other metallic structures, whether cathodically protected or not, may be located in relatively close proximity to one or more sources of time varying electromagnetic fields. Steel pipelines, for example, are often located underneath high power transmission lines. Accordingly, the testing of cathodic protection systems may include testing or monitoring for AC effects including any AC voltages or currents induced in the cathodically protected structure. In at least one embodiment disclosed herein, a single coupon package includes, in addition to a test coupon (also referred to herein as a DC coupon) and a native coupon, a third coupon, referred to herein as an AC coupon, to monitor the effects of AC fields and further includes a reference electrode. Moreover, in at least one embodiment, a disclosed coupon package employs an AC coupon with a surface area that differs from the surface areas of other coupons in the coupon package. A coupon package disclosed herein, designed for use with a single test station, addresses cost issues associated with the historical use of different test stations for different coupons and measurement accuracy issues associated with the historical use of a reference cell deployed at the surface.

In one embodiment, a test coupon package for a CPS includes a reference electrode connected to a reference probe input, a first active coupon connected to a first probe input, a second active coupon connected to a second probe input, and a native coupon connected to a third probe input. A surface area of the second active coupon that will contact the electrolytic medium may, in one embodiment, be substantially less than a surface area of the first active coupon that will contact the electrolytic medium. In another embodiment, the first active coupon is electrically connected to the pipeline during at least a portion of operation of the CPS and the second active coupon is electrically connected to the pipeline during at least a portion of testing.

The surface area of the first active coupon and a surface area of the native coupon will contact the electrolytic medium and, in some embodiments, are approximately the same size. In at least one embodiment, the surface area of the first active coupon exceeds the surface area of the second active coupon by a factor equal to or exceeding 100 and the surface area of the second active coupon is approximately 1 $cm^2$. The test coupon package may include a cylindrical housing and in some embodiments, the first active coupon and the native coupon may include steel rings circumventing the cylindrical housing. In some embodiments, the reference electrode is positioned between the first active coupon and the native coupon and electrically non-conductive spacers separate the reference electrode from the first active coupon and the native coupon. In at least one embodiment, the first active coupon and the native coupon are positioned between the second active coupon and the reference electrode and electrically non-conductive spacers separate each of the reference electrode, the first active coupon, the native coupon, and the second active coupon from one another. A surface area of the reference electrode may, in some embodiments, exceed the surface area of the first active coupon. A conical nose piece connected to the cylindrical housing may be included in some embodiments and the second active coupon may, in at least one of these embodiments, be attached to the test coupon package at a narrow end of the conical nose piece such that only one surface of the second active coupon is configured to contact the electrolytic medium.

In at least one embodiment, the reference electrode includes a copper-copper sulfate electrode. In some embodiments, a test block includes a reference probe input configured to connect to a reference electrode of a test coupon package, a first coupon input configured to connect to a first active coupon of the test coupon package, a second coupon input configured to connect to a second active coupon of the test coupon package, a third coupon input configured to connect to a native coupon of the test coupon package, and a first auxiliary input, configured to connect to a first point of a pipeline and to a second contact of a switch configured, when closed, to connect the pipeline and the first active coupon. In some embodiments, a surface area of the second active coupon that will contact an electrolytic medium is substantially less than a surface area of the first active coupon that will contact the electrolytic medium.

A second auxiliary input connected to a second point of the pipeline, different than the first point of the pipeline may be included in some embodiments. An anode input connected to the second contact of the switch and further configured to connect to an anode may be included in some embodiments. In at least one embodiment, the first coupon input is connected to a first contact of the switch and the switch is configured, when closed, to connect the first contact and the second contact. The switch may, in some embodiments, be manually controlled and the test block may include a manually operated switch controller.

In one embodiment, a method for testing a CPS includes performing an ON potential test, comprising, measuring a DC voltage between a test probe input and a reference probe input of a test block (wherein the test probe input is configured to connect to a test coupon of a test coupon package and the reference probe input is configured to connect to a reference electrode of the test coupon package), closing a switch to connect a first contact connected to the test coupon and a second contact connected to a pipeline, measuring the voltage between the test probe input and the reference probe input to measure the "ON" potential, performing a NATIVE potential test, including measuring a DC voltage between a native probe input of the test block and the reference probe input (wherein the native probe input is configured to connect to a native coupon of the test coupon package and the reference probe input is configured to connect to the reference electrode of the test coupon package) and measuring the voltage between the native probe input and the reference probe input to measure the "NATIVE" potential, and performing an AC current density test, including measuring an AC current passing through an AC probe input configured to connect to an AC coupon and a first pipeline probe input configured to connect to the pipeline, opening the switch, and converting the measured AC current to an AC current density.

In at least one embodiment of the method, the AC coupon has a smaller surface area that will contact an electrolytic medium than a surface area of the test coupon that will contact the electrolytic medium. In some embodiments, the method includes performing an AC potential test including measuring an AC potential between the reference electrode and the test coupon. In at least one embodiment, the method may include converting the measured AC current to a current density which includes dividing the AC current by a surface area of the AC coupon (wherein the surface area of the AC coupon is 1 $cm^2$). In some embodiments, the method includes performing an instant off potential test, including after measuring the ON potential, opening the switch, and within approximately 1500 milliseconds of opening the switch, measuring the DC voltage.

In the following description, details are set forth by way of example to facilitate discussion of the disclosed subject matter. It should be apparent to a person of ordinary skill in the field, however, that the disclosed embodiments are exemplary and not exhaustive of all possible embodiments. Throughout this disclosure, a hyphenated form of a reference numeral refers to a specific instance of an element and the un-hyphenated form of the reference numeral refers to the element generically or collectively. Thus, for example, widget 12-1 refers to an instance of a widget class, which may be referred to collectively as widgets 12 and any one of which may be referred to generically as a widget 12.

FIG. 1 depicts elements of an embodiment of a cathodic protection test system 100 that may be used in conjunction with a cathodically protected metallic structure buried in soil. In the embodiment of cathodic protection test system 100 illustrated in FIG. 1, the metallic structure is a steel pipeline 110 and cathodic protection test system 100 includes a test block 111, a coupon package 101, and a number of electrically conductive interconnects 120 electrically connecting coupon package 101 to test block 111. The embodiment of coupon package 101 illustrated in FIG. 1 includes a reference electrode 102 and three (3) coupons. The coupons included in the coupon package 101 illustrated in FIG. 1 include a test coupon 104, a native coupon 106, and an AC coupon 108.

The cathodic protection test system 100 illustrated in FIG. 1 includes interconnects 120 between each of the coupons and a corresponding probe input 130 on test block 111. Interconnections 120 may be copper wires or cables. In the illustrated embodiment, test coupon 104 is connected to test probe input 130-4 via interconnect 120-4, native coupon 106 is connected to native probe input 130-6 via interconnect 120-6, and AC coupon 108 is connected to AC probe input 130-8 via interconnect 120-8. In the cathodic protection test system 100 illustrated in FIG. 1, test coupon 104 is also connected to a first terminal of a switch 135 on test block 111 via an interconnect 120-9. The switch 135 illustrated in FIG. 1 includes a second terminal connected to a first auxiliary (AUX1) probe input 130-5. In the depicted embodiment, first auxiliary probe input 130-5 is connected to pipeline 110 via interconnect 120-5 and second auxiliary (AUX 2) probe input 130-7 is connected to pipeline 110 via interconnect 120-7. As illustrated in FIG. 1, first auxiliary probe input 130-5 is also connected to an anode probe input 130-3, which is shown connected to an anode 113 via interconnect 120-3. In at least one embodiment, anode 113 is an optional and additional AC interference reduction feature.

FIG. 1 further illustrates a reference probe input 130-2 connected to a reference electrode 102 on coupon package 101 via interconnect 120-2. In at least one embodiment, reference electrode 102 is an electrochemically stable material with respect to the electrolytic medium. In the case of a soil medium, reference electrode 102 may be a copper-copper sulfate electrode or another suitable material. Cathodic protection test system 100 enables a user to measure voltage between the reference electrode 102 and any of the coupons 104, 106, and 108, with or without a direct connection between pipeline 110 and test coupon 104 via switch 135. Cathodic protection test system 100 also enables the user to measure current between pipeline 110 and test coupons 104 or 108. As depicted in FIG. 1, test coupon 104 may be electrically connected to pipeline 110 via switch 135 and first auxiliary probe input 130-5. While not depicted, in one embodiment AC coupon 108 may be electrically connected to pipeline 110 directly or via test coupon 104 or switch 135. In at least one embodiment, test coupon 104 may be electrically connected to pipeline 110 during at least a portion of operation of a CPS and AC coupon 108 may be electrically connected to pipeline 110 during at least a portion of operating cathodic protection test system 100.

Figure 2A:
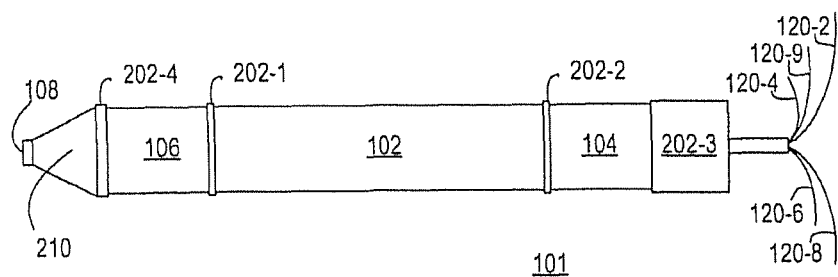
FIG. 2A is a side view of a coupon package suitable for use in conjunction with a cathodic protection test system.

Referring to FIG. 2A, one embodiment of coupon package 101 is illustrated. As illustrated in FIG. 2A, coupon package 101 is a substantially cylindrical structure that incorporates multiple steel ring coupons that circumvent the circular coupon package housing. As illustrated in FIG. 2A, coupon package 101 includes native coupon 106 disposed adjacent to reference electrode 102, which itself is adjacent to test coupon 104. Electrically nonconductive spacers 202 may be disposed at each end of coupons 104 and 106 and also at each end of reference electrode 102. The coupon package 101 illustrated in FIG. 2A includes a conical nose piece 210 extending from an end of the cylindrical housing nearest to native coupon 106. In other embodiments (including an embodiment depicted in FIG. 2C and FIG. 2D), the order in which coupons 104 and 106 and reference electrode 102 are arranged, the width of nonconductive spacers 202, the cylindrical housing end to which conical nose 210 is attached, and the cylindrical housing end to which AC coupon 108 is attached may differ from the embodiment depicted in FIG. 2A and FIG. 2B.

Figure 2B:
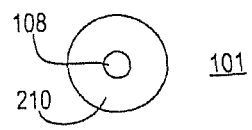
FIG. 2B is a front view of the coupon package of FIG. 2A.
Figure 2C:
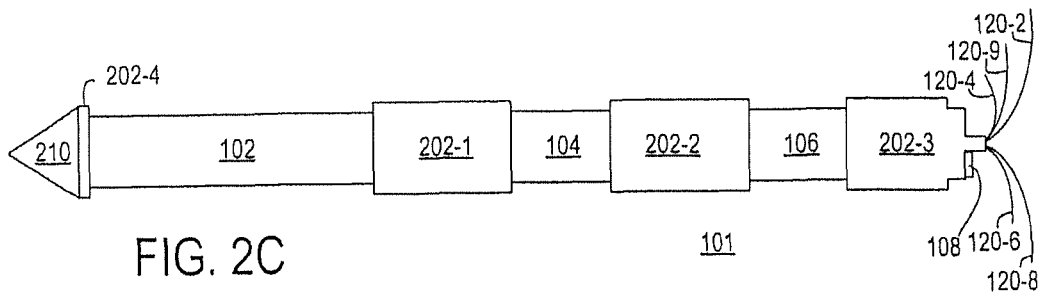
FIG. 2C is a side view of another coupon package suitable for use in conjunction with a cathodic protection test system.
Figure 2D:
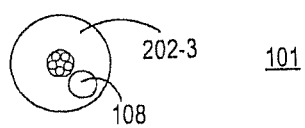
FIG. 2D is a front view of the coupon package of FIG. 2C.

Coupon packages 101 depicted in FIGS. 2A and 2C include a third coupon, AC coupon 108. In the illustrated embodiment of FIG. 2A, AC coupon 108 is located inside a narrow end of conical nose piece 210 such that only one surface of AC coupon 108 is in contact with the surrounding soil when coupon package 101 is installed in the field. In the illustrated embodiment of FIG. 2C, AC coupon 108 is located inside nonconductive spacer 202-3 such that only one surface of AC coupon 108 is in contact with the surrounding soil when coupon package 101 is installed in the field. FIG. 2B shows a front view of the FIG. 2A coupon package. FIG. 2D shows a front view of the FIG. 2C coupon package. Although FIGS. 2A and 2C are not necessarily to scale, each emphasizes nevertheless that, in the depicted embodiment of coupon package 101, when coupon package 101 is installed in the field, test coupon 104 and native coupon 106 may be approximately equal in the surface area contacting the surrounding soil, while AC coupon 108 may have a substantially smaller surface area contacting the surrounding soil than either of the other two coupons.

Interconnects 120 illustrated in FIG. 2A include AC coupon interconnect 120-8, native interconnect 120-6, reference electrode interconnect 120-2, a live wire interconnect 120-9 for test coupon 104, and an auxiliary wire interconnect 120-4 for test coupon 104. The interconnects depicted in FIG. 2A correspond to like numbered interconnects depicted in FIG. 1.

As suggested above, at least one embodiment of coupon package 101 as illustrated in FIG. 2A includes coupons having different surface areas and includes two active coupons (104, 108) in addition to native coupon 106 and reference electrode 102.

The coupon package 101 illustrated in FIG. 2A includes test coupon 104 having the same or similar surface area as native coupon 106. In at least one embodiment, test coupon 104 and native coupon 106 have the same surface area, which may be 100 times greater than the surface area of AC coupon 108. In one exemplary embodiment, test coupon 104 has a diameter of approximately 2 inches, a length of approximately 2.5 inches along the cylindrical axis of coupon package 101, and a surface area of approximately 100 $cm^2$. In the depicted embodiment, native coupon 106 has the same dimensions and the same surface area as test coupon 104. The reference electrode 102 illustrated in FIG. 2A may have a lesser diameter than test coupon 104, but since it may be anywhere from 5 to 10 inches in overall length along the cylindrical axis, it has a greater surface area than test coupon 104. The AC coupon 108 may, in this embodiment, have a 1 $cm^2$ surface area. In at least one embodiment, an outer diameter of coupon package 101 is approximately 2 inches.

Interconnects 120 illustrated in FIG. 2C include AC coupon interconnect 120-8, native interconnect 120-6, reference electrode interconnect 120-2, a live wire interconnect 120-9 for test coupon 104, and an auxiliary wire interconnect 120-4 for test coupon 104. The interconnects 120 depicted in FIG. 2C correspond to like numbered interconnects depicted in FIG. 1.

As suggested above, at least one embodiment of coupon package 101 as illustrated in FIG. 2C includes test coupons having different surface areas and includes two active coupons (104, 108) in addition to native coupon 106 and reference electrode 102.

The coupon package 101 illustrated in FIG. 2C includes test coupon 104 having the same or similar surface area as native coupon 106. In at least one embodiment, test coupon 104 and native coupon 106 have the same surface area, which may be 100 times greater than the surface area of AC coupon 108. In one exemplary configuration, test coupon 104 has a diameter of approximately 2 inches, a length of approximately 2.5 inches along the cylindrical axis of coupon package 101, and a surface area of approximately 100 $cm^2$. In the depicted embodiment, native coupon 106 has approximately the same dimensions and the same surface area as test coupon 104. The reference electrode 102 illustrated in FIG. 2C has the same or similar diameter as test coupon 104, but since its length along the cylindrical axis is longer than that of test coupon 104, it has a greater surface area than test coupon 104. The AC coupon 108 may, in this embodiment, have a 1 cm² surface area. In at least one embodiment, an outer diameter of coupon package 101 is approximately 2 inches and each of nonconductive spacers 202-1, 202-2, and 202-3 have a length of between approximately 2.5 inches and 3 inches along the cylindrical axis of coupon package 101.

Figure 3:
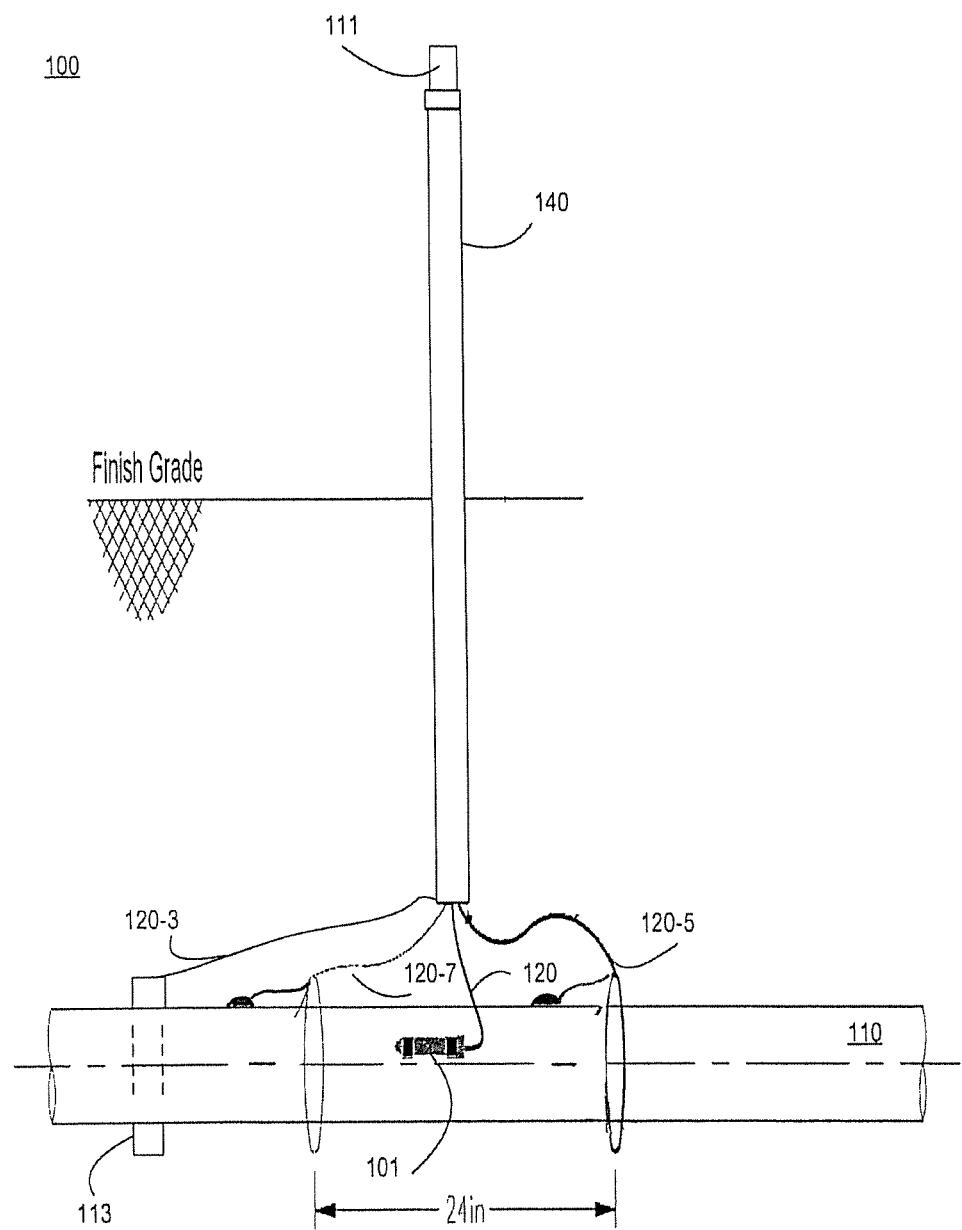
FIG. 3 illustrates a cathodic protection test system installed in the field.

FIG. 3 illustrates cathodic protection test system 100 installed in the field with a coupon package 101 buried below grade and connected through interconnects 120 to test block 111, which is located above grade. In the FIG. 3 illustration, interconnects 120 travel from coupon package 101 through a test block riser 140 from below grade to test block 111. FIG. 3 further illustrates interconnect 120-5 connecting between test block 111 and pipeline 110. In the FIG. 3 implementation, a second interconnect 120-7 represents a second auxiliary connection to pipeline 110 from test block 111. Interconnects 120-5 and 120-7 connecting to pipeline 110 are illustrated as forming a loop around pipeline 110 before attaching to pipeline 110. In at least one embodiment, a displacement 142 between the loops formed by interconnects 120-5 and 120-7 may be approximately 24 inches. Coupon package 101 is illustrated oriented parallel to pipeline 101 positioned at a depth that is equal to or approximately equal to a depth of a centerline of pipeline 110.

Figure 4:
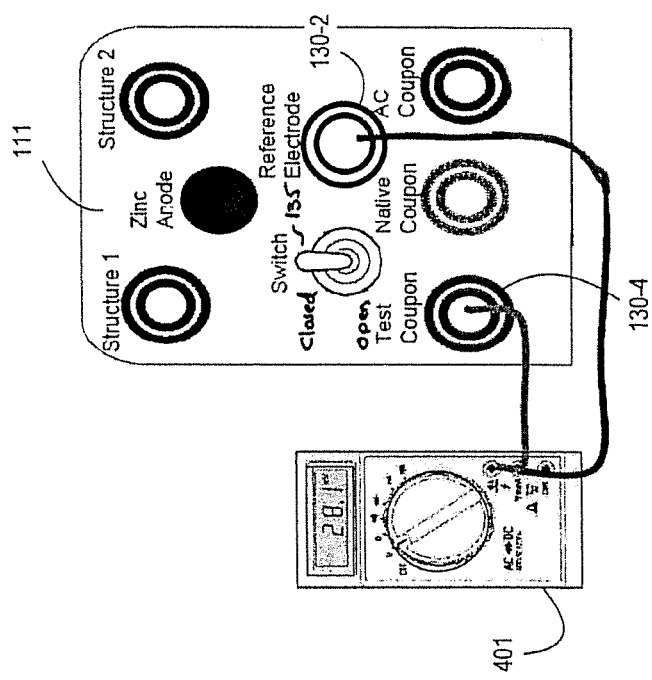
FIG. 4 illustrates a use of a cathodic protection test system to measure "on" potential and "instant off" potential.

FIG. 4 illustrates a DC testing configuration in which a multimeter 401 is connected to test coupon probe 130-4 and reference electrode probe 130-2. To test the "on" potential, multimeter 401 is switched to read DC voltage (in millivolts for example) and the switch 135, which may be a single pole single throw, normally closed switch, is placed in a closed position so that pipeline 110 is connected to test coupon 104 through switch 135 via interconnects 120-9 and 120-5. In this configuration, the multimeter 401 will display the "on" potential of test coupon 104. If the switch 135 is placed in the open position so that the interconnection between pipeline 110 and test coupon 104 is opened, the multimeter 401 will display the "instant off" or "polarized" potential of test coupon 104 during an interval from approximately 500 to 1500 milliseconds after switch opening.

Figure 5:
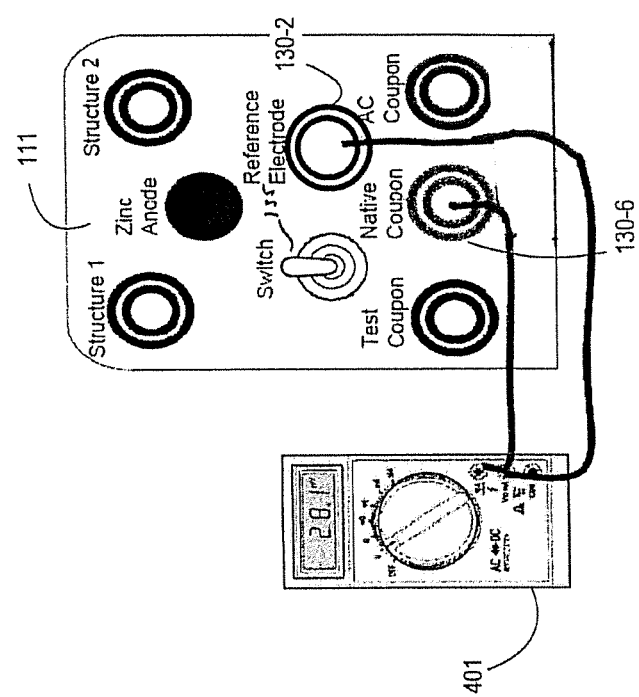
FIG. 5 illustrates a use of a cathodic protection test system to measure native state potential.

FIG. 5 illustrates a configuration for testing "native state" potential in which multimeter 401 is set to measure DC millivolts and the multimeter's negative and positive inputs are connected to reference electrode probe 130-2 and native coupon probe 130-6, respectively. In this configuration, the multimeter will indicate the "native state" potential of native coupon 106.

Figure 6:
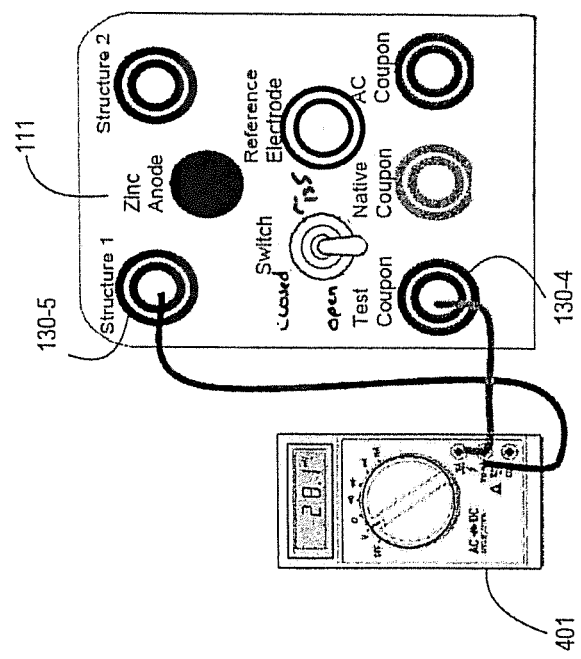
FIG. 6 illustrates a use of a cathodic protection test system to measure DC current density.

FIG. 6 illustrates a configuration for measuring DC current density in which the multimeter 401 is set to measure DC current (in milliamps for example) and the multimeter negative input is connected to first auxiliary probe 130-5 while the multimeter positive input is connected to test coupon probe 130-4. As illustrated in FIG. 6, the switch 135 is turned to the open or off position to measure the DC current magnitude and polarity. Because the surface area of test coupon 104 is known, the measured current can be readily converted to a current density by dividing the measured current by the surface area of the coupon. Moreover, by employing a coupon with a power-of-ten surface area, e.g., 1, 10, 100, or 1000 cm², the multimeter reading in amps can be converted to a current density reading simply by adjusting the decimal point and/or units.

Figure 7:
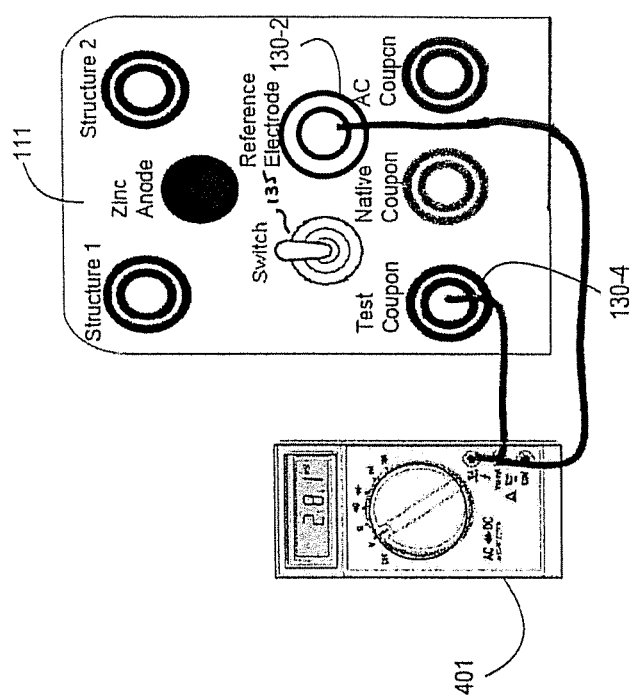
FIG. 7 illustrates a use of a cathodic protection test system to measure AC potential.

FIG. 7 illustrates a configuration to test a coupon's AC potential in which multimeter 401 is set to read AC voltage (in millivolts for example) and the negative input is connected to reference electrode probe 130-2 while the positive input is connected to test coupon probe 130-4 and the switch 135 is placed in the closed position.

Figure 8:
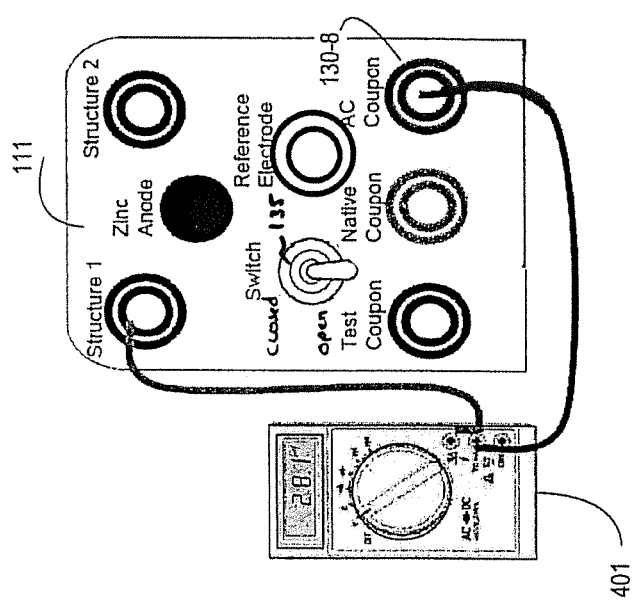
FIG. 8 illustrates a use of a cathodic protection test system to measure AC current density.

FIG. 8 illustrates a configuration for testing AC current density in which multimeter 401 is connected between the first auxiliary probe 130-5 and AC coupon probe 130-8. The switch 135 is switched to the open or off position and the multimeter is set to read AC current in milliamps. The multimeter reading can then be converted to a current density by dividing the measured current by the surface area. In the exemplary embodiment in which the surface area of AC coupon 108 is 1 cm², the AC current density is determined by multiplying the measured AC current expressed in amperes by $10^4$ to obtain the current density in terms of amps per square meter.

To the maximum extent allowed by law, the scope of the present disclosure is to be determined by the broadest permissible interpretation of the following claims and their equivalents, and shall not be restricted or limited to the specific embodiments described in the foregoing detailed description.

What is claimed is:

1. A test coupon package for a cathodic protection system including a pipeline buried in an electrolytic medium, the test coupon package comprising:
   a reference electrode connected to a reference probe input;
   a first active coupon connected to a first probe input;
   a second active coupon connected to a second probe input; and
   a native coupon connected to a third probe input;
   wherein a surface area of the second active coupon that will contact the electrolytic medium is substantially less than a surface area of the first active coupon that will contact the electrolytic medium.

2. The test coupon package of claim 1, wherein the first active coupon is electrically connected to the pipeline during at least a portion of operation of the cathodic protection system and the second active coupon is electrically connected to the pipeline during at least a portion of testing.

3. The test coupon package of claim 1, wherein the surface area of the first active coupon and a surface area of the native coupon that will contact the electrolytic medium are approximately the same.

4. The test coupon package of claim 1, wherein the surface area of the first active coupon exceeds the surface area of the second active coupon by a factor equal to or exceeding 100 and further wherein the surface area of the second active coupon is approximately 1 cm2.

5. The test coupon package of claim 1, wherein the test coupon package comprises a cylindrical housing and wherein the first active coupon and the native coupon comprise steel rings circumventing the cylindrical housing.

6. The test coupon package of claim 5, wherein the reference electrode is positioned between the first active coupon and the native coupon and wherein electrically non-conductive spacers separate the reference electrode from the first active coupon and the native coupon.

7. The test coupon package of claim 5, wherein the first active coupon and the native coupon are positioned between the second active coupon and the reference electrode and wherein electrically non-conductive spacers separate each of the reference electrode, the first active coupon, the native coupon, and the second active coupon from one another.

8. The test coupon package of claim 5, wherein a surface area of the reference electrode exceeds the surface area of the first active coupon.

9. The test coupon package of claim 5, further comprising:
a conical nose piece connected to the cylindrical housing, wherein the second active coupon is attached to the test coupon package at a narrow end of the conical nose piece, wherein only one surface of the second active coupon is configured to contact the electrolytic medium.

10. The test coupon package of claim 1, wherein the reference electrode comprises a copper-copper sulfate electrode.

11. A test block for testing a cathodic protection system, the test block comprising:
a reference probe input configured to connect to a reference electrode of a test coupon package;
a first coupon input configured to connect to a first active coupon of the test coupon package;
a second coupon input configured to connect to a second active coupon of the test coupon package, wherein a surface area of the second active coupon that will contact an electrolytic medium is substantially less than a surface area of the first active coupon that will contact the electrolytic medium;
a third coupon input configured to connect to a native coupon of the test coupon package; and
a first auxiliary input, configured to connect to a first point of a pipeline and to a second contact of a switch configured, when closed, to connect the pipeline and the first active coupon.

12. The test block of claim 11, further comprising:
a second auxiliary input connected to a second point of the pipeline, different than the first point of the pipeline.

13. The test block of claim 11, further comprising:
an anode input connected to the second contact of the switch and further configured to connect to an anode.

14. The test block of claim 11, wherein the first coupon input is connected to a first contact of the switch and wherein the switch is configured, when closed, to connect the first contact and the second contact.

15. The test block of claim 14, further comprising, wherein the switch is manually controlled and wherein the test block further comprises a manually operated switch controller.

* * * * *